United States Patent [19]  
Aslanian et al.

[11] 4,294,246  
[45] Oct. 13, 1981

[54] FLOW CONTROL DEVICE FOR ADMINISTRATION OF INTRAVENOUS FLUIDS

[75] Inventors: Jerry L. Aslanian, Phoenix; Jody L. Numbers, Scottsdale, both of Ariz.

[73] Assignee: Master Medical Corporation, Phoenix, Ariz.

[21] Appl. No.: 5,313

[22] Filed: Jan. 22, 1979

[51] Int. Cl.³ .............................................. A61M 5/00
[52] U.S. Cl. ................................................. 128/214 E
[58] Field of Search ............... 128/214 R, 274, 214.2, 128/214.4, 214 C; 251/205, 203

[56] References Cited

U.S. PATENT DOCUMENTS

| | | | |
|---|---|---|---|
| 2,980,392 | 4/1961 | Greenwood | 251/205 |
| 3,384,338 | 5/1968 | Dermody | 251/205 |
| 3,408,040 | 10/1968 | Kraft | 251/203 |
| 3,410,521 | 11/1968 | Sowers et al. | 251/205 |
| 3,785,378 | 1/1974 | Stewart | 128/214 C |

Primary Examiner—Robert W. Michell  
Assistant Examiner—Thomas Wallen  
Attorney, Agent, or Firm—Gregory J. Nelson

[57] ABSTRACT

A metering apparatus for controlling the administration of intravenous fluids (IV) having a flow passage within a housing connectable to a source of IV fluid and to a delivery tube terminating at an administration needle. The flow passageway incorporates a valve seat. A metering pin is axially moveable within the passage and relative to the valve seat. The metering pin defines a flow passageway and a variable area flow notch which are positionable relative to the valve seat to regulate flow from a purge to a flow blocking position. In the preferred embodiment, positioning of the metering pin is accomplished by a cam engaging a portion of the pin forming a cam follower. The cam is manually adjustable by a dial on the device to accomplish accurate, repeatable and continuous flow adjustment over the full range. In other embodiments, the pin may be adjusted relative to the valve seat by a rack and pinion arrangement and other mechanical equivalents.

4 Claims, 19 Drawing Figures

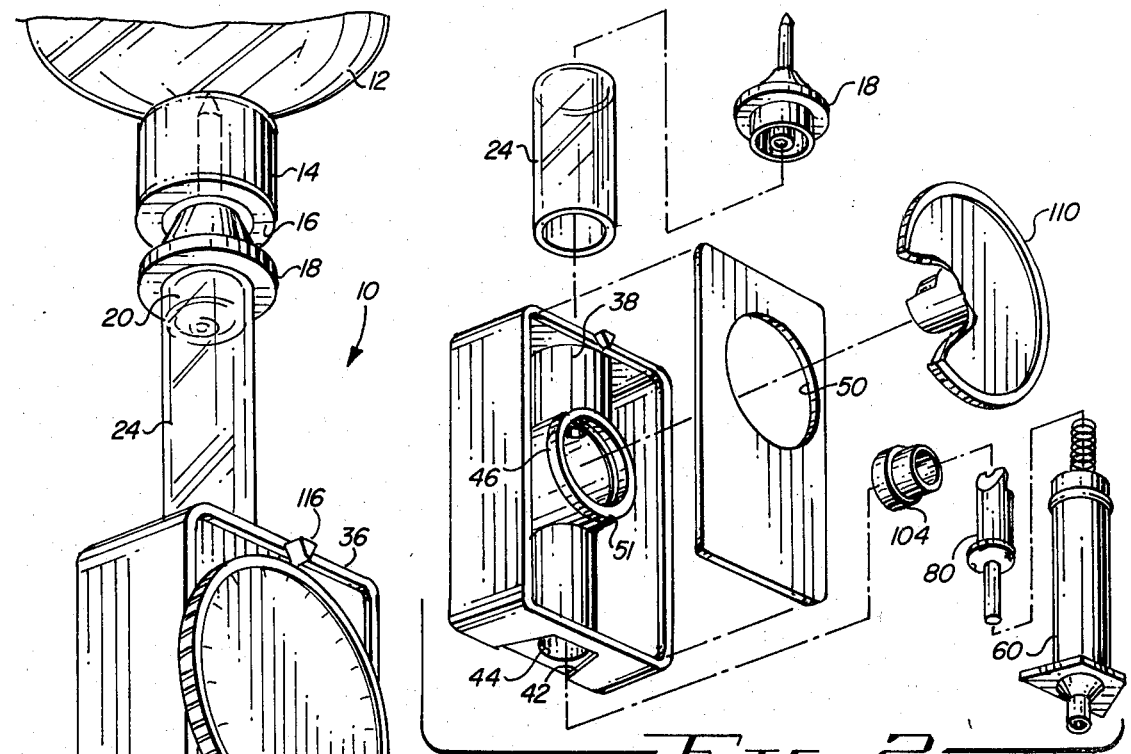
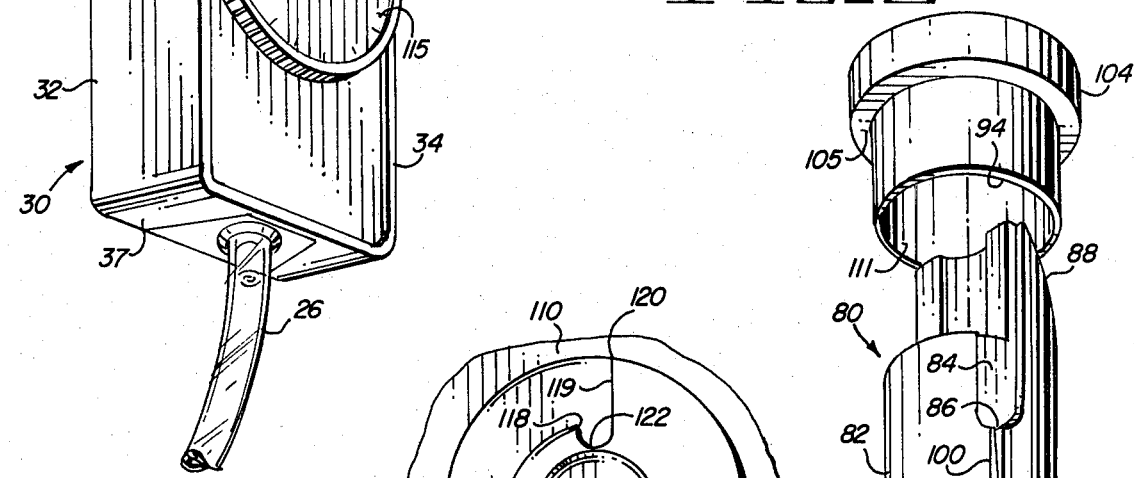
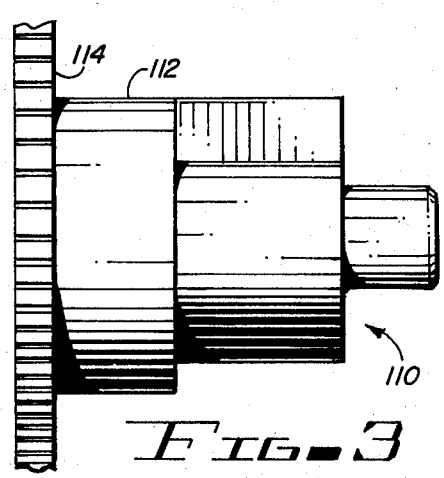
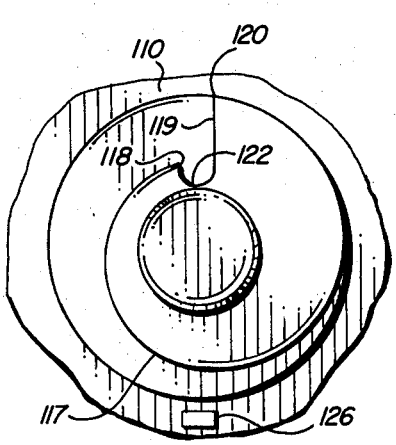
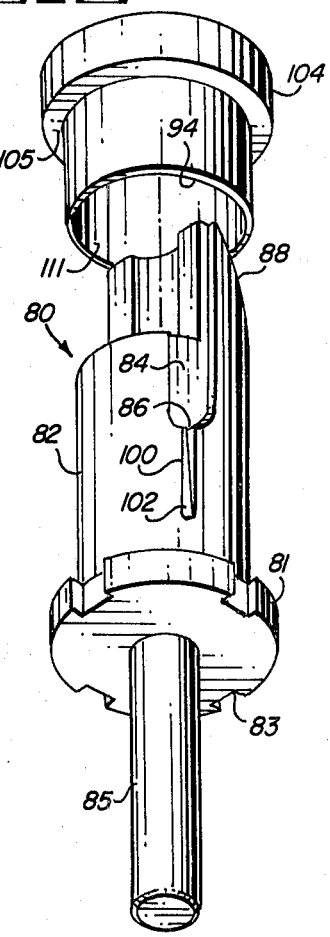

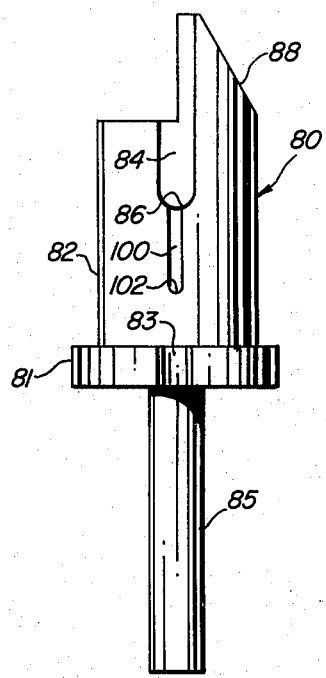
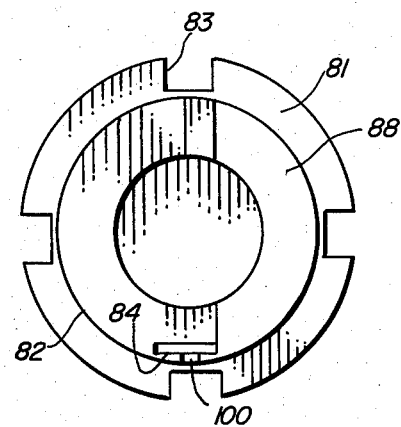
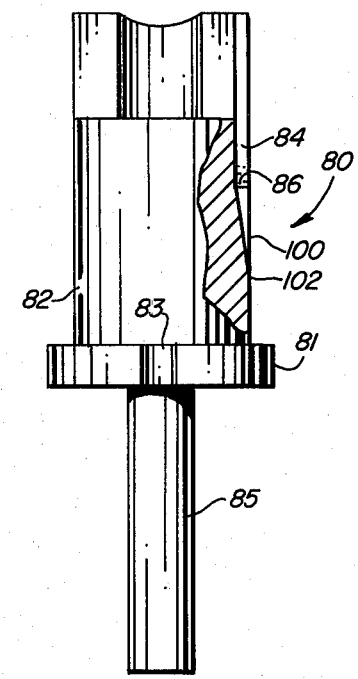
FIG.-6   FIG.-8   FIG.-7
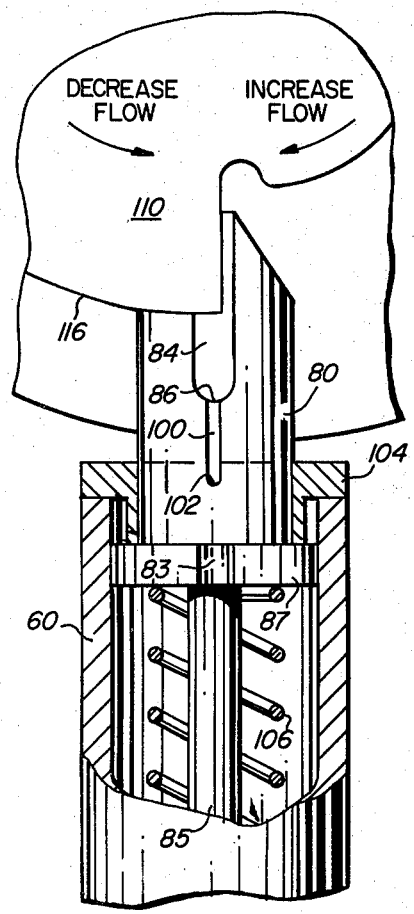
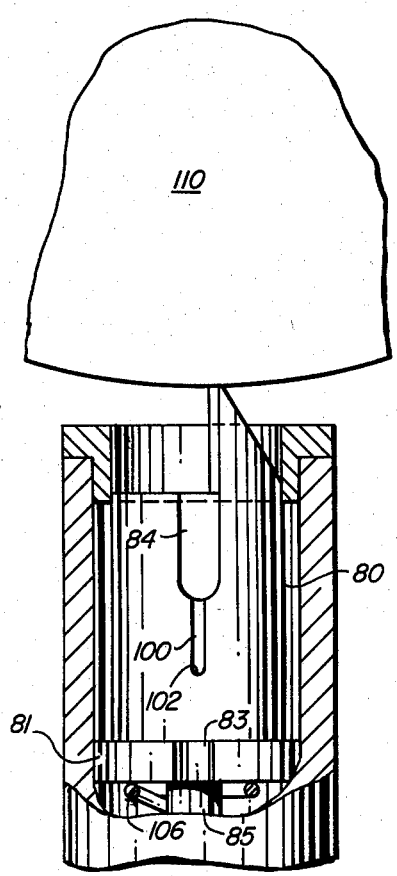
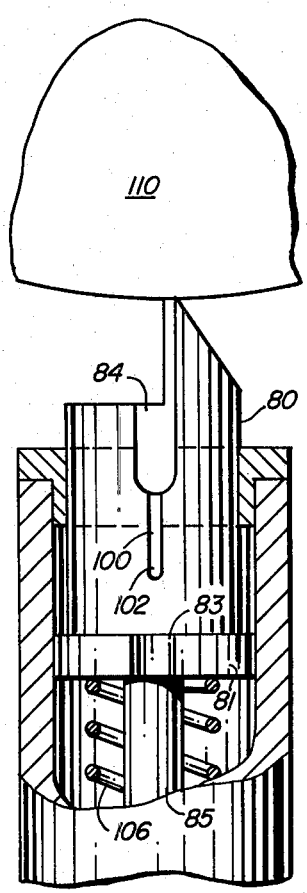
FIG.-9A   FIG.-9B   FIG.-9C

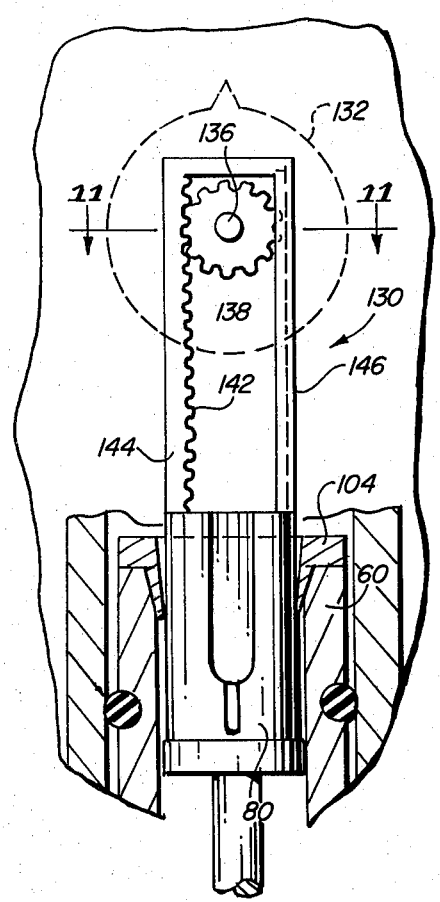
FIG-10
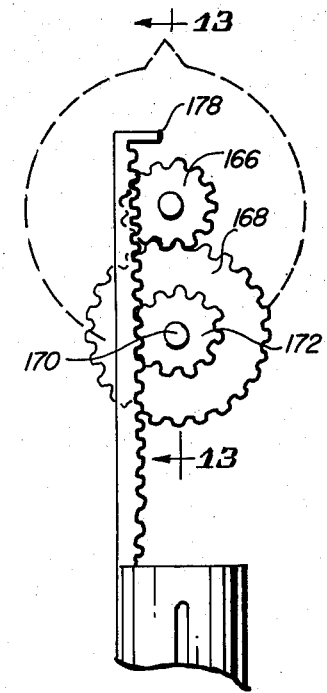
FIG-12
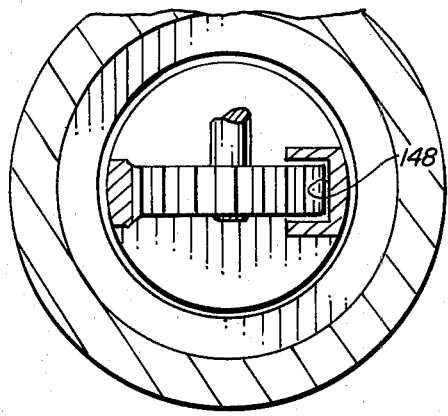
FIG-11
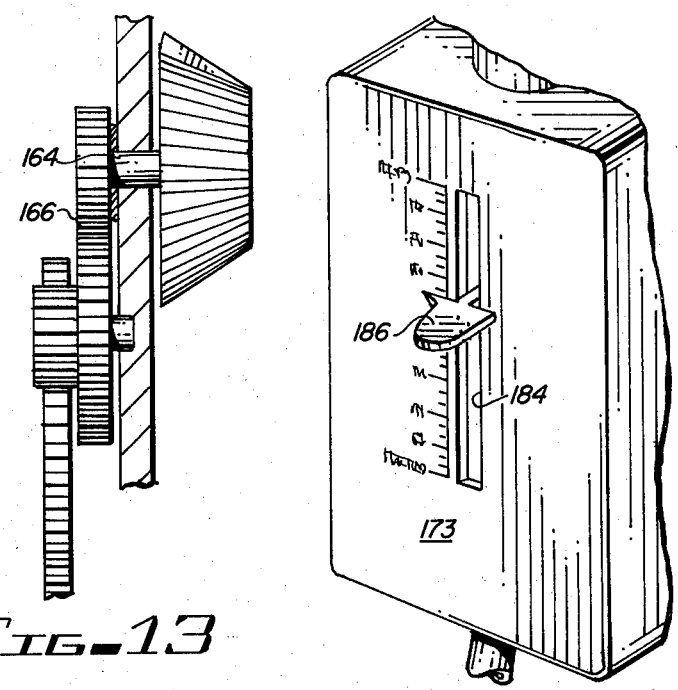
FIG-13
FIG-14
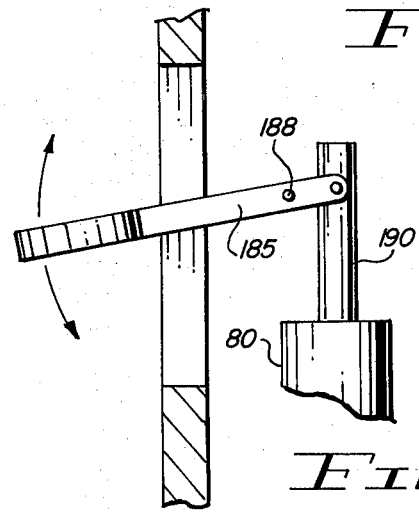
FIG-15

FLOW CONTROL DEVICE FOR ADMINISTRATION OF INTRAVENOUS FLUIDS

The present invention relates to a device for regulator controlling the flow of intravenous (IV) or parenteral fluids. More particularly, the present invention relates to a flow metering device for precisely establishing and maintaining a preselected flow rate during the administration of IV liquids at the patient.

The administration of fluids by intravenous infusion is a common medical procedure. Representative intravenous fluids include blood, plasma, dextrose and isotonic saline solutions. IV infusions are generally carried out with the container of IV fluid suspended above the patient. Customarily such containers have a seal which is broken by the insertion of a piercer or "spike" and the fluid is delivered to the patient at an administration needle through a drip chamber and flexible tubing connected to the container at the spike. The purpose of the drip chamber is to facilitate the determination of the flow or drip rate through the tubing. The infusion rate is generally varied or regulated by use of a pinch valve or roller clamp associated with the tubing.

Initially when infusions are carried out, the tubing and needle are initially purged of air by initiating a flow of fluid through the tubing. The needle is then inserted into a vena puncture site at a suitable location such as one of the veins in the wrist area and infusion is initiated. Preferably, when the vena puncture occurs in the lower arm of the patient, the arm should be properly stabilized in a contoured IV arm support. Medical personnel administering the IV will close the pinch valve or roller clamp to restrict the IV tubing and the number of drops passing through the drip tube are counted. The appropriate flow rate is established by trial and error method by progressively restricting or opening the tubing by means of the pinch valve.

The administration procedure described requires the attention of the nurse or physician for a substantial time. The time is required not only in the initial establishment of the proper flow rate but continual monitoring is required. It is the general practice of many medical facilities to require a nurse or physician to periodically check the flow rate by counting drops at the drop chamber. In addition to the procedure requiring substantial time, the method of regulating flow by means of a manual clamp secured to the drip tubing is extremely inaccurate. Temperature changes will cause expansions and contractions of the IV tubing permitting the flow rate to vary. Tubing may lose "memory" and collapse under continuous squeezing necessitating constant re-adjustments of the initial setting. Roller clamps or pinch valves of the type described have a tendency to slip off which can in some cases be extremely dangerous to the patient. If an inadvertant and sudden increase in flow of IV fluid is encountered, the patient can go into "speed shock". Obviously, flow decreases are similarly undesirable in treating a patient. Some independent tests have shown that conventional pinch valves and roller clamps maintain flow only within about 25% accuracy thereby requiring constant re-adjustment. It will be appreciated that controlling infusion rates to the desired degree of accuracy by conventional pinch valves and roller clamps is extremely difficult even with constant attention on the part of attending medical personnel.

Various expedients have been resorted to in an effort to correct the problem set forth above. Flow regulating devices of various types have been developed and can be found in the prior art. For example, U.S. Pat. No. 3,785,378 to Stewart shows a valve for the administration of intravenous fluids which has an annular member forming a central passage through which fluid is flowable to an end face with multiple grooves. The inner ends of the grooves communicate with the passage and a flow control member is rotatable to place a flow port successively and selectively in communication with the grooves to vary the flow rate.

Another approach to the problem is found in U.S. Pat. No. 3,877,428 to Seagle et al which shows an infusion control device for selectively controlling the rate of administration of fluids parenterally to a patient. The control device is attachable along the IV tube and includes a rotatable metering plate defining a capillary flow path between the input and the output of the control device. A metering plate is axially rotatable with respect to the input and output ports to vary the effective length of the flow path so as to regulate flow between full flow and zero flow conditions.

A somewhat similar approach is shown in U.S. Pat. No. 3,880,401 which discloses a flow metering valve having inner and outer component parts which are movable relative one to another at screw threads to effect relative axial movement of a metering valve plug in and out of a metering bore of regulating and terminating flow through the valve flow passage.

While all of the forementioned devices are substantial improvements over the roller clamp or pinch valve type of arrangement traditionally used, these devices impose certain problems. The prior art devices, due to their construction, present problems in manufacture making them impractical in many instances. Devices of the aforementioned type generally require the attending nurse or physician to operate the device with both hands which is often awkward and may therefore require two medical personnel in attendance for set-up and purge procedures. Further, these devices do not always provide the constancy and repeatability of flow rates desired by medical personnel.

Briefly, the present invention overcomes the problems and provides a novel infusion control device which can be adjusted to maintain various settings from zero to full flow conditions with repeatability. The invention provides precise, and continuous and infinite variable control over the flow of fluid. The flow rate may be changed by the attendant by simply moving a control member, an operation which may be performed with one hand. Briefly, in the preferred embodiment, the flow control device of the present invention comprises a housing which contains an axially extending sleeve. A metering tube including a valve seat portion, is received within the sleeve and defines a fluid passageway. A metering pin is axially movable relative to the seat and is provided with a flow passageway including a variable area notch. One end of the sleeve is connectable to a drip chamber and the lower end of the tube terminates in a male coupling or nipple which is attachable to IV tubing. Flow adjusting means serve to position the metering pin relative to the valve to adjust fluid flow through the flow passageway. In the preferred embodiment of the invention, the flow adjustment means comprises a cam which cooperates with a follower on the metering pin. The cam is rotated by means of a dial exteriorly of the valve housing. In other embodiments, the flow adjusting means may comprise a rack and pinion or plunger mechanism operatively connected to the metering pin.

The above and other objects and advantages of the present invention will become more readily apparent from the following description, claims and drawings in which:

FIG. 1 is a perspective view of the flow regulating device of the present invention shown in position connected to an IV bottle;

FIG. 2 is an exploded perspective view of the flow regulating device of the present invention;

FIG. 3 is a side elevational view of the cam shown in FIG. 2;

FIG. 4 is a plan view of the cam surface;

FIG. 5 is an enlarged perspective view of the metering pin and associated valve seat;

FIG. 6 is an elevational view of the metering pin showing the flow passageway;

FIG. 7 is a front elevational view of the metering pin;

FIG. 8 is a top view of the metering pin;

FIG. 9A is a partial sectional view illustrating the flow regulating device with the metering pin in a flow blocking position;

FIG. 9B is a partial sectional view of the device in a metering or flow controlling position;

FIG. 9C is a partial sectional view of the device in a metering or flow controlling position;

FIG. 10 is a side elevational view showing a rack and pinion for adjusting the position of the metering pin;

FIG. 11 is a sectional view taken along lines 11—11 of FIG. 10;

FIG. 12 is a side view showing adjustment means connected to the metering pin in the form of a gear reduction system;

FIG. 13 is a sectional view taken along lines 13—13 of FIG. 12;

FIG. 14 is a perspective view of still another embodiment of the control device of the present invention;

FIG. 15 is a partial side elevational view showing still another form of the metering pin adjustment means used with the embodiment shown in FIG. 14.

Figure 9:
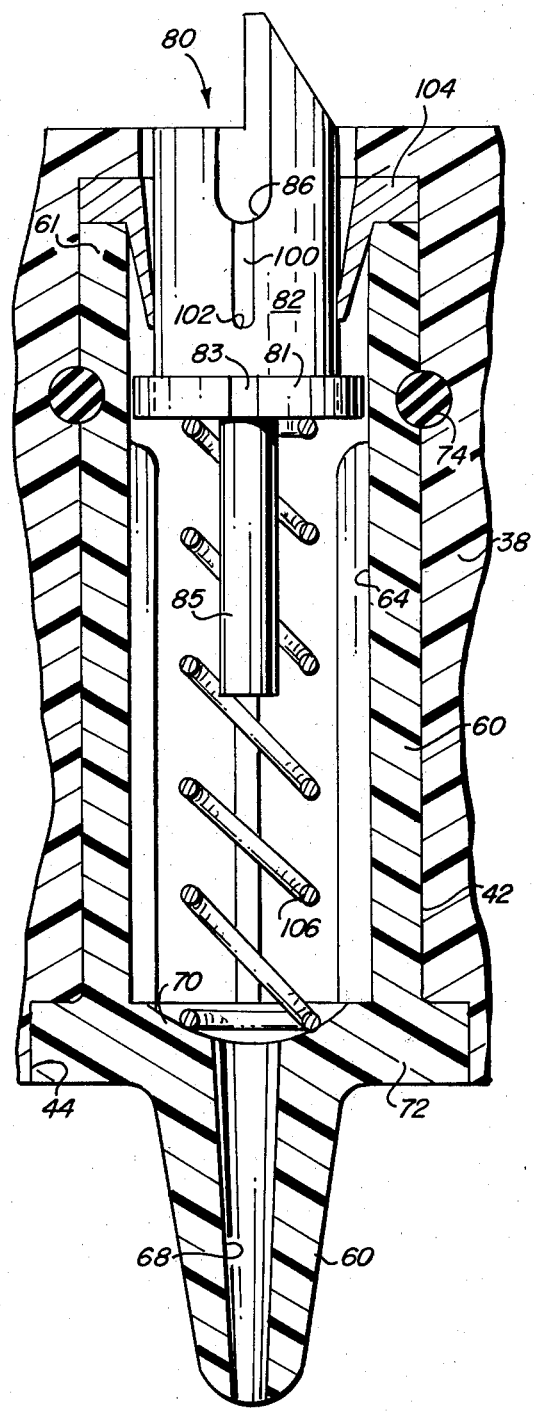
FIG. 9 is a view, partly in section, illustrating the metering tube and pin assembly.
Figure 16:
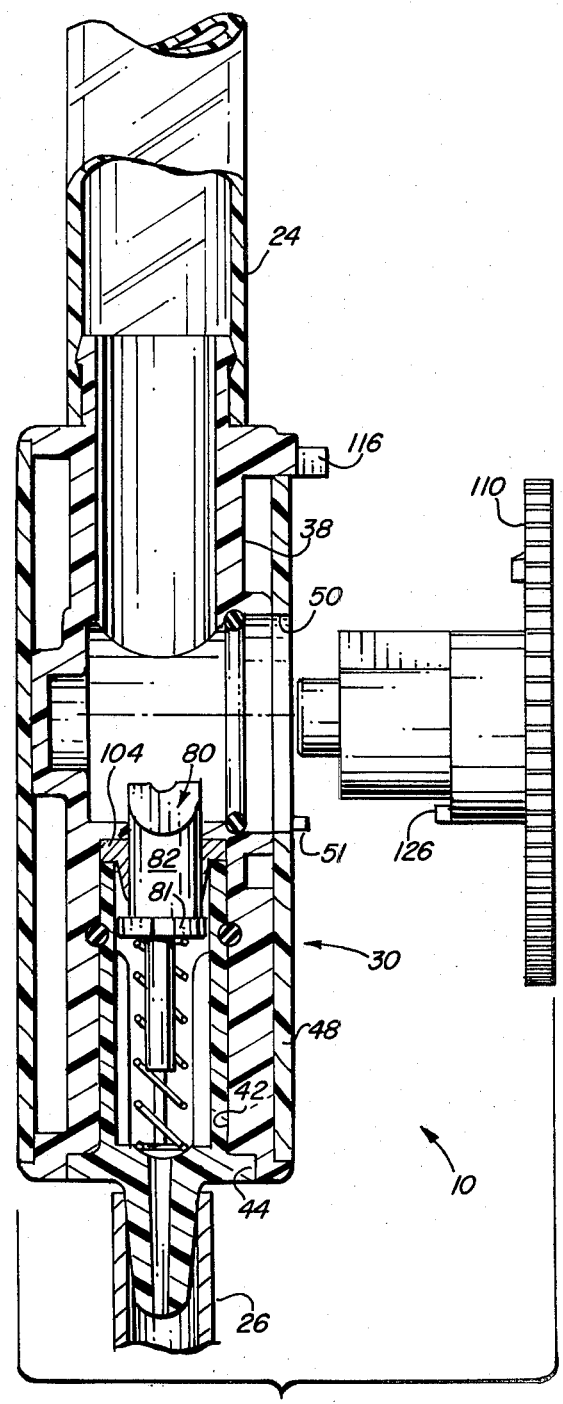
FIG. 16 is a sectional view of the device.

Turning now to the drawings, FIG. 1 generally shows the flow control device of the present invention which is designated by the numeral 10. Flow control device 10 is shown connected in an IV system including a bottle or container 12 of an appropriate IV solution such as plasma, blood, dextrose or saline solution. Bottle 12 terminates at an outlet 14 which is sealed by a plug or stopper 16. A piercing spike 18 is inserted through the stopper or closure 16 which has cylindrical projection 20 which receives drip chamber 24. Various IV systems conventionally may be open or closed. In some cases the spike or piercer 18 may be vented through an appropriate filter media to admit air into the bottle 12. The flow regulating device 10 of the present invention is shown interposed between the drip chamber 24 and IV tubing 26 which terminates at an IV administration tip or needle, not shown.

The details of construction of the IV control device 10 are best seen in FIGS. 2 through 7. Control device 10 includes a generally rectangular body or housing 30 having opposite side walls 32 and 34 and top and bottom 36 and 37, respectively.

A channel 38 having a cylindrical bore 44 extends axially between top and bottom walls 36 and 37 and opens at the top and bottom walls. Drip chamber 24 is connectable at the top end of channel 38 at top wall 36 at an appropriate fitting. A recess 42 is provided in bottom wall 37 extending about bore 44.

An annular hub 46 intercepts cylindrical channel 38 intermediate end walls 36 and 37 dividing the channel into upper and lower sections. Cover plate 48, which is generally rectangular in configuration, is positionable over the face of the housing 48 engaging the edges of the side and end walls. Plate 48 is provided with a circular cut-out 50 receiving the upper edge of hub 46. Plate 48 can be secured in place by any convenient means such as by mechanical fastening means or adhesive bonding. A projection 51 which serves as a stop, as will be more fully explained, extends from hub 51.

Metering tube 60 is inserted in the lower portion of cylindrical channel 38 and has an upper edge 61 and terminates in channel 38 at a location below hub 46. Metering tube 60 defines an interior cylindrical bore 64.

The lower end of metering tube 60 terminates at a nipple or coupling 66 which is connectable to IV tubing 26. Coupling or nipple 36 defines an axial passageway 68 which communicates with bore 64. Passage 68 is of smaller diameter than bore 64 so that an annular surface 70 is defined at the lower end of bore 64. A generally trapezoidal flange 72 projects from the lower end of tube 60 corresponding and shaped to configuration of recess 44.

Annular sealing member 74 is integrally formed or is placed about tube 60 and, as best seen in FIG. 9, forms a fluid or hydrostatic seal between the exterior of the metering tube 60 and the interior of cylindrical channel 38.

Metering or control of flow is achieved by axial displacement of metering pin 80 relative to valve seat 104. Pin 80 is best shown in FIGS. 5 to 8. Metering pin 80 has a generally cylindrical body 82 which terminates at upper end at a projection 88. Projection 88 defines a cam follower surface as will be more fully described. A circular flange 81 projects from the lower end of body 82 and is provided with a series of peripheral flow grooves 83. The diameter of the circular flange 81 closely corresponds to the inner diameter of metering tube 60 and is selected to permit metering pin 80 to slide axially within the tube. A guide pin 85 extends axially from flange 81.

Flow through the device is directed along flow passage 84 which extends axially along the outer surface of body 82 terminating at lower end wall 86 at an intermediate location. The cross-sectional configuration of the flow passage 84 may vary but the passage is shown as having a flat bottom and spaced apart vertical side walls with the width of the passage being several times the depth. A metering notch 100 communicates with flow passage 82 at end wall 86. Metering notch 100 preferably decreases or tapers in cross-sectional area having a maximum cross-sectional area at its upper end where the notch intercepts end wall 86 and diminishes or decreases in area downwardly terminating at end 102 at a location above flange 81. The notch 100 may be of various cross-sectional shapes but is shown as being configured to decrease in depth axially proceeding towards flange 81. Notch 100 may also be of uniform depth having a decreasing width or, in some cases, may decrease in both width and depth. It is also possible to reverse the orientation of the flow passage and metering notch with the direction of operation being accordingly reversed.

Valve seat 104 is shown as a cylindrical insert which cooperatively fits into a recess provided at the upper end of metering tube or sleeve 60. Valve seat 104 is provided with a bore 94 having lower edge 111 which forms a valving surface which cooperates with metering pin 80 to regulate or meter flow through the control device. Valve seat 104 is held in place in sleeve or tube 60 by annular shoulder 105.

In an assembled position, as seen in FIG. 9, metering pin 80 is slideably received within bore 64 of tube 62. Tube 62 is in turn, positioned in the lower portion of channel 38. A biasing compression spring 106 extends from end 70 of the bore 64 at the bottom of the metering tube and engages the under side of flange or disc 81 of metering pin 80 extending circumferentially about axial pin 85. Spring 106 urges or biases the metering pin upwardly placing the cam follower 88 in contact with cam 110.

Cam 110 is best shown in FIGS. 3 and 4 and includes a cylindrical hub 112 which is rotatably received within hub 46 of housing 30. A circular dial 114 is secured to cylindrical journal 112 and is positioned at the face of the unit 10. Preferably the peripheral edges of dial 114 are serrated for improved gripping characteristics. As shown in FIG. 1, dial 114 also extends laterally beyond the opposite side walls 32 and 34 of the dial housing to facilitate manipulation of the dial with one hand. The outer surface of dial 114 is suitably graduated or calibrated with numerical or other indicia 115 to indicate appropriate flow rates. The calibrations are cooperatively read in conjunction with pointer 116 centrally positioned on the face of the housing at the front edge of top wall 36.

Cam 110 includes a cam surface 117 which is generally spiral in configuration extending from low point 118 through rise 119 to high point 120. A lug or projection 126 is provided on the inner face of the dial 114 and is engageable with projection 51 on hub 46 to restrict the rotation of the cam in both directions of rotation. Notch 122 is provided in the cam surface intermediate points 118 and 120 and will engage follower 88 of the metering pin in the "off" position.

The various components described above are assembled in a manner as best seen in FIGS. 2, 5 and 9 with the metering pin inserted in the lower portion of cylindrical channel 38 in the housing 30. The metering pin is slideable within bore 64 of sleeve 62 with flange 81 engaging the bore 64. The upper end of the metering tube is received within valve seat 104. The cam assembly 110 is positioned within the housing, the journal being rotatable within hub 46 and sealed by elastomeric O-ring 125.

FIGS. 9A, 9B and 9C best illustrate the relative position of the metering pin and cam in various operating positions from a stop to a purge position. These figures are viewed from the face or front of the device 10 with the cam illustrated in dotted lines for convenience. As is shown in FIG. 1, the control device 10 is first connected in an IV system to a drip chamber 24 terminating at a spike or piercing device 18 which is inserted into the stopper 16 of a container or bottle containing an appropriate IV solution. The IV tubing 24 terminates at an administration tip and connected to the control device 10 at coupling 66. Generally dial 114 will be positioned in the "off" position with the appropriate indicia 115 aligned with marker or pointer 116. In this position, the stop or projection 126 on the inner surface of the dial 126 engages the cooperative projection at 51 on hub 46 so that further counter clockwise rotation as viewed in FIG. 9A is restricted. Cam follower 88 is engaged in cam notch 122. In the position shown in FIG. 9A, all flow through the device is stopped. Fluid entering the control device 10 through drip chamber 24 flows through upper delivery tube 38 where it will be blocked by the outer diameter of pin 80 and seat 104.

Prior to attaching the needle to the tubes, the attendant will rotate dial 114 clockwise until pointer 116 aligns with indicia 115 indicating a purge position. Rotation of dial 114 will, in turn, rotate the cam surface 116 clockwise as viewed in FIGS. 9A through 9C to axially depress the metering pin 80 against the force of spring 106. Metering pin 80 will be displaced to the position shown in FIG. 9B which positions the lower end 86 of flow passageway 84 below the lower edge of valve seat 104. This permits flow in upper delivery section of channel 38 to flow or bridge the valve seat through the larger area flow passageway and across slot 83 in flange 81. The flow is then directed to the lower end of the valve tube 60, through the IV tubing 24 to the administration tip. The purge condition is generally maintained for a brief period of time (approximately 30 cc fluid is usual recommended quantity to purge through system) so that all air is purged from the system prior to infusion. Dial 114 will then be returned to the off position shown in FIG. 9A which allows the metering pin to move axially upwardly terminating flow through the unit.

The needle can then be inserted into the patient at the vena puncture site and the needle attached to the tubing at a hub or fitting. Dial 114 is then rotated until the appropriate flow rate is achieved. In the delivery or metering position as shown in FIGS. 9C, the variable metering notch 100 may be variously positioned with respect to the lower edge 111 of the valve seat 104. Accordingly, the metering notch provides for progressive and almost infinite selection of flow rates from full on to off depending on the relative position of the metering notch and the lower edge 110 of the valve seat. For example, as the lower end 102 of the metering notch 100 approaches lower edge 111 of the valve seat, flow is progressively restricted. As more of the metering notch 100 is extended below edge 110, the flow rate increases. Thus accurate flow rates can be precisely delivered with determinable repeatability by selective positioning of the metering pin by means of the dial and cam assembly. Flow rates can be stopped, decreased or increased selectively by rotation of the dial and cam assembly.

Thus the successive and selective registration of the metering pin and valve seat contributes to the desired predeterminable flow rate function of the valve. The particular configuration of the metering notch and groove may vary as pointed out above, it being only necessary to have a substantially unrestricted section and a section of varying area. With the particular arrangement shown, the desired flow rate can be achieved reducing the risk of inaccurate fluid drip rate administration to the patient.

It is noted that the construction shown herein has a unique safety feature which prevents the unit from delivering IV fluid at a rate greater than the selected rate therefore minimizing the risk of infusing the patient with fluid at an excessive rate which can cause speed shock and can be extremely dangerous to the patient. Note that if the cam as shown in FIGS. 1 to 9 is set at a predetermined rate, the biasing spring 106 always urges the metering pin 80 upwardly into contact with the cam surface 117. This means that the biasing spring continually biases the metering pin towards the closed position and in the event of some malfunction, metering pin 80 will be urged upwardly to a decreased or off position so that the unit cannot deliver at a rate greater than the pre-set or established rate.

Another significant safety feature of the present invention is that the device allows the administrator of the IV a reference point for checking accuracy of flow rates to the patient. Once the dial is set, a pre-determined flow can be expected. If that flow rate is not achieved, as determined by a visual count, then the attendant should check for any problems such as blocked or crimped tubing and correct needle position in the vein. Improper needle position may occlude the cannula and impede flow temporarily. A change of position by the patient can result in a sudden flow increase when the occlusion is removed. With the device of the present invention, the attendant should be able to detect and remedy any such positional problems reducing danger of inaccurate infusion rates to the patient.

The control device of the present invention also lends itself to other means for positioning of the metering pin 80 within the valve seat 104 and metering tube 60. For example, FIGS. 10 and 11 show inclusion of a rack and pinion instead of a cam for progressive positioning of the metering pin. In FIGS. 10 and 11, the metering pin 80 is axially movable within tube 60 by means of a rack and pinion arrangement generally designated by the numeral 130. The structure of the metering pin 80, tube 62 and valve seat 104 which performs the valving or metering function are essentially the same as has been described with previous figures and further detailed description is not deemed necessary with reference to these figures.

The rack and pinion arrangement 130 includes a dial 132 which is mountable at the exterior of the instrument housing. A shaft 136 extends into the flow passageway defined by channel 38. The inner end of shaft 136 carries pinion gear 138. Pinion gear 138 engages teeth 142 of linear rack 144 which extends axially from the upper end of pin 80. A guide channel 146 is spaced apart in parallel relationship with rack 144 and defines slot 148 which receives the periphery of the teeth of gear 126 as the gear rotates. An upper stop member 150 extends transversely between channel 146 and rack 144. It will be obvious that as dial 132 is rotated, motion will be imparted to the metering pin 80 through rack and pinion 134 and 128 and that the metering pin may be selectively positioned relative to valve seat 104 to regulate or meter flow as has been described.

FIGS. 12 and 13 show still another arrangement for axial advancement and retraction of pin 80. The embodiment shown in FIGS. 12 and 13 is generally designated by the numeral 160 and includes a dial 162 mounted for rotation in the housing of the device. A shaft 164 extends into the flow passageway of channel 38. The inner end of shaft 164 carries small diameter gear 166 which, in turn, drives larger gear 168. Gear 168 is mounted on shaft 170. Gear 172 is mounted on common shaft 170 with gear 168. Gear 172 is in engagement with teeth 176 of linear rack 174. A stop 178 extends from the upper end of rack 174. The gear train comprising gear 166, gear 168, gear 172 and rack 174 serves as a reduction system to provide more precise positioning of the metering pin. One complete revolution of gear 166 will impart only a partial revolution to gear 170 based on the ratio of the number of teeth between gears 168 and 166 which is translated to axial movement of pin 80 by rack 174. As mentioned above, the gear reduction system provides for a more precise positioning of the metering pin as is required.

Still another means of positioning the metering pin 80 is shown in FIGS. 14 and 15. In these figures, the instrument housing 180 has a face plate 172 provided with an axial slot 184. An actuating lever 185 extends through slot 184 and is pivotally mounted within the housing at pivot point 188. An indicator 186 on the outer end of lever 185 cooperates within indicia along slot 184. The inner end of lever 185 is attached to plunger 190 connected to metering pin 80. The position of pivot point 188 is displaced toward plunger 190 so that linear movement of indicator 186 results in a small proportional movement at plunger 184. This results in preciseness of setting and permits the attendant to more accurately position the metering pin.

In the description of the embodiments shown in FIGS. 9 to 15, certain details have been omitted for purposes of clarity. It is understood the metering pin and cooperating valve seat are as have been described with reference to previous figures.

It will be obvious to those skilled in the art that other means may be used to advance and retract the metering pin within the valve to perform the metering function. For example, it is possible to utilize engageable threaded members which may be rotated to result in relative axial movement of the metering pin to the valve seat.

The IV control valve of the present invention can be inexpensively manufactured of any suitable materials such as ABS or similar plastic materials. Because of the simplicity of construction and the relative small number of parts, the device can be designed as a disposable unit. The device would be preferably autoclaved or gas sterilized and provided to the ultimate user in a sterilized package for attachment in an IV system. When IV administration is complete, the entire unit including the drip chamber, control device, administration tip and tube can be disposed of to minimize cross-contamination and for efficient labor saving practice. The device of the present invention preferably can be manufactured in a compact size such that the unit can be grasped in one hand by the attendant. The dial member being relatively large and preferably extending beyond the lateral sides of the instrument housing facilitates operation in one hand. This allows the attendant to make any necessary adjustments with one hand and, as an independent check of flow rates, to easily time flow rates by reading a wrist watch or other timing instrument held or worn on the other hand.

Accordingly, from the foregoing, it is understood that accurately and highly predictable and repeatable flow rates can be achieved by a positioning the metering pin with respect to the valve seat to vary the flow area through the valve.

The invention may be embodied in other specific forms without departing from the spirit and scope of the present invention. It will be obvious to those skilled in the art to make various changes and modifications to the embodiments described herein without departing from the spirit or essential characteristics of the invention. To the extend that these changes, alterations and modifications do not depart from the spirit and scope of the appended claims they are intended to be encompassed therein.

We claim:

1. A metering device for accurately setting flow rates in an IV system including a source of IV or parenteral fluid, said valve comprising:
   (a) a housing;
   (b) a fluid passageway within said housing;
   (c) a valve seat in said passageway having a valving surface;
   (d) a cylindrical metering member axially moveable relative to said valve seat, said metering member including a cam follower and said member further defining a flow passage in the wall surface having a cross-sectional area which varies axially along at least a section of said flow passage;
   (e) actuating cam means having a generally spiral cam surface cooperable with said cam follower;
   (f) biasing means urging said metering member into engagement with said cam surface in a direction to reduce flow; and
   (g) dial means moveable relative to said housing for imparting rotational movement to said actuating cam means whereby said cam surface axially displaces said member relative to said valving seat surface to progressively regulate flow from a closed to a purge position with flow metering occurring along said portion of said flow passage which varies in cross-sectional area.

2. The metering valve of claim 1 wherein said dial means comprises a circular member having a diameter greater than the transverse dimension of said housing.

3. The metering valve of claim 1 wherein said flow passageway includes a first section of generally uniform cross-section and a second section having an axially downward decreasing cross-section and whereby:
   (a) full flow or purge occurs when said first section bridges said valve seat surface;
   (b) metering occurs when said second section bridges said valve surface; and
   (c) flow is blocked when neither section bridges said surface.

4. The metering valve of claim 3 wherein said cam surface is configured to decrease flow as said metering member moves in a direction opposing said biasing force.

* * * * *